(12) United States Patent
Seth

(10) Patent No.: US 10,765,436 B2
(45) Date of Patent: Sep. 8, 2020

(54) TOURNIQUET

(71) Applicant: Ajay K. Seth, North Canton, OH (US)

(72) Inventor: Ajay K. Seth, North Canton, OH (US)

( * ) Notice: Subject to any disclaimer, the term of this patent is extended or adjusted under 35 U.S.C. 154(b) by 0 days.

(21) Appl. No.: 15/455,817

(22) Filed: Mar. 10, 2017

(65) Prior Publication Data

US 2018/0256173 A1 Sep. 13, 2018

(51) Int. Cl.
*A61B 17/32* (2006.01)
*A61B 17/132* (2006.01)
*A61B 90/00* (2016.01)

(52) U.S. Cl.
CPC .. *A61B 17/1322* (2013.01); *A61B 2090/0808* (2016.02)

(58) Field of Classification Search
CPC .. A61F 2013/00468; A61F 2013/00565; A61F 2013/00561; A61F 2013/00127; A61F 2013/00421; A61F 2013/00463; A61F 2013/00655; A61F 2013/00089; A61F 2013/00174; A61F 2013/0028; A61B 17/1327; A61B 17/132; A61B 17/135; A61B 17/1322
USPC .......................................................... 606/203
See application file for complete search history.

(56) References Cited

U.S. PATENT DOCUMENTS

| | | | |
|---|---|---|---|
| 6,545,193 B1 * | 4/2003 | Morgenstern | A61F 13/0273 128/876 |
| 8,465,514 B1 | 6/2013 | Rose | |
| 2002/0052570 A1 * | 5/2002 | Naimer | A61F 13/0273 602/53 |
| 2007/0250109 A1 * | 10/2007 | Kerstein | A61B 17/1322 606/203 |
| 2013/0304113 A1 * | 11/2013 | Eikman | A61B 17/1322 606/203 |
| 2015/0209052 A1 * | 7/2015 | Hopman | A61B 17/1325 606/203 |

FOREIGN PATENT DOCUMENTS

| | | |
|---|---|---|
| AU | 2013100587 A4 | 5/2013 |
| WO | WO 2012/088027 A2 | 6/2012 |
| WO | WO 2015/085124 A2 | 6/2015 |

OTHER PUBLICATIONS

International Search Report and Written Opinion for Application No. PCT/US2018/021914, dated Jun. 11, 2018.
International Preliminary Report on Patentability for Application No. PCT/US2018/021914, dated Sep. 10, 2019.

* cited by examiner

*Primary Examiner* — Katrina M Stransky
*Assistant Examiner* — Brigid K Byrd
(74) *Attorney, Agent, or Firm* — JK Intellectual Property Law, PA

(57) ABSTRACT

A tourniquet for a limb may include an elongated band with first and second ends, a central portion between the first and second ends, and first and second edges extending between the first and second ends. The elongated band defines an opening between the first and second edges spaced from the first end for receiving the second end and the central portion, thereby forming a loop along the elongated band beginning at the opening and ending at a point on the elongated band passing through the opening.

13 Claims, 5 Drawing Sheets

TOURNIQUET

TECHNICAL FIELD

The present disclosure relates generally to a tourniquet and more particularly to a tourniquet that can be applied to a person's body part such as a limb by that person.

BACKGROUND

Tourniquets may be used in case of severe injury to a limb to prevent blood loss. Tourniquets are placed around the limb and tightened. Some tourniquets are tightened as applied while others are applied and then tightened. Tourniquets are intended only for temporary use, and are often employed by emergency personnel prior to further treatment of an injury. Tourniquets are also carried by military personnel, hunters, hikers, etc., in case of injury in locations remote from healthcare providers.

Some tourniquets are designed to be applied by the person with the injury. In such devices, the tourniquets can be applied using one hand, for example, to stop bleeding on the arm opposite that hand.

While existing devices generally perform as required, some take longer than optimally desired to apply and tighten, require multiple steps to apply and tighten, do not deploy into a uniform configuration along the limb, and/or do not securely stay in a tightened position. Accordingly, a tourniquet addressing one or more of the above drawbacks, and/or providing other benefits, would be welcome.

SUMMARY

According to certain aspects of the disclosure, a tourniquet for a limb may include an elongated band having a first end, a second end, and a central portion between the first end and the second end, the elongated band having a first edge and a second edge opposite the first edge extending between the first end and the second end. The elongated band defines an opening therethrough between the first edge and the second edge spaced from the first end, the opening configured for receiving the second end and the central portion therethrough so as to form a loop along the elongated band beginning at the opening and ending at a point on the elongated band passing through the opening. A gripping element is located at the second end of the elongated bond, the gripping element extending at least substantially between the first edge and the second edge. The gripping element is more rigid than the elongated band so as to reinforce the elongated band during tightening of the band around the limb. Various options and modifications are possible.

According to other aspects of the disclosure, a tourniquet for a limb may include an elongated band having a first end, a second end, and a central portion between the first end and the second end, the elongated band having a first edge and a second edge opposite the first edge extending between the first end and the second end. The elongated band defines an opening therethrough between the first edge and the second edge spaced from the first end, the opening configured for receiving the second end and the central portion therethrough so as to form a loop along the elongated band beginning at the opening and ending at a point on the elongated band passing through the opening. Co-operating fastener elements are disposed along an upper surface and a lower surface of the elongated band located proximate the second end so as to assist in holding the elongated band in place around the limb. Various options and modifications are possible.

According to other aspects of the disclosure, a tourniquet for a limb may include an elongated band having a first end, a second end, and a central portion between the first end and the second end, the elongated band having a first edge and a second edge opposite the first edge extending between the first end and the second end. The elongated band defines an opening therethrough between the first edge and the second edge spaced from the first end, the opening configured for receiving the second end and the central portion therethrough so as to form a loop along the elongated band beginning at the opening and ending at a point on the elongated band passing through the opening. A first visible directional indicator is located on an upper surface of the elongated band proximate the first end to highlight the first end. Various options and modifications are possible.

According to other aspects of the disclosure, a tourniquet for a limb may include an elongated band having a first end, a second end, and a central portion between the first end and the second end, the elongated band having a first edge and a second edge opposite the first edge extending between the first end and the second end. The elongated band defines an opening therethrough between the first edge and the second edge spaced from the first end, the opening configured for receiving the second end and the central portion therethrough so as to form a loop along the elongated band beginning at the opening and ending at a point on the elongated band passing through the opening. The width is greater proximate the opening than at least some other locations along the elongated band from the first end to the second end. Various options and modifications are possible.

According to certain other aspects of the disclosure, a tourniquet for a limb may include an elongated band having a first end, a second end, and a central portion between the first end and the second end, the elongated band having a first edge and a second edge opposite the first edge extending between the first end and the second end. The elongated band defines an opening therethrough between the first edge and the second edge spaced from the first end, the opening configured for receiving the second end and the central portion therethrough so as to form a loop along the elongated band beginning at the opening and ending at a point on the elongated band passing through the opening. Co-operating fastener elements disposed along an upper surface and a lower surface of the elongated band located proximate the first end so as to assist in holding the elongated band in a spiral-wound configuration with the second end in the middle and the first end on the outside. Various options and modifications are possible.

According to other aspects of the disclosure, a tourniquet for a limb may include an elongated band having a first end, a second end, and a central portion between the first end and the second end, the elongated band having a first edge and a second edge opposite the first edge extending between the first end and the second end. The elongated band defines an opening therethrough between the first edge and the second edge spaced from the first end, the opening configured for receiving the second end and the central portion therethrough so as to form a loop along the elongated band beginning at the opening and ending at a point on the elongated band passing through the opening. An attachment member is secured to the elongated band for attaching the elongated band to an external item when the elongated band is in a spiral-wound configuration with the first end in the middle and the second end on the outside. Various options and modifications are possible.

BRIEF DESCRIPTION OF THE DRAWINGS

More details of the present disclosure are set forth in the drawings.

DETAILED DESCRIPTION

Figure 1:
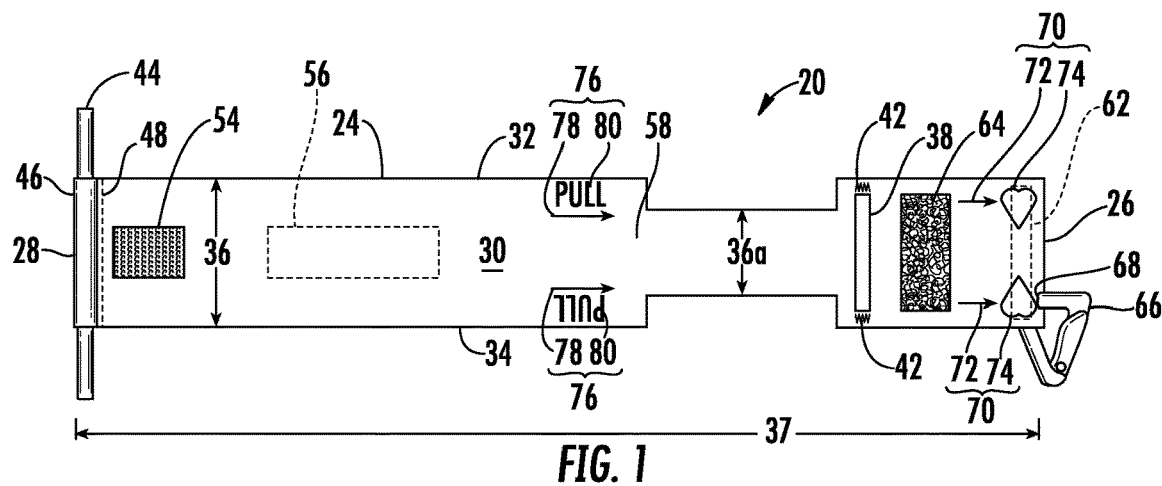
FIG. 1 is a top view of a tourniquet according to certain aspects of the present disclosure in an unrolled and unlooped condition.
Figure 2:
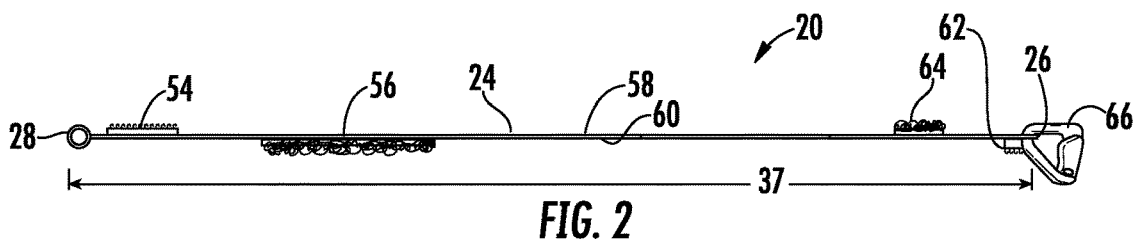
FIG. 2 is a side view of the tourniquet of FIG. 1.

Detailed reference will now be made to the drawings in which examples embodying the present disclosure are shown. The detailed description uses numeral and letter designations to refer to features in the drawings. Like or similar designations in the drawings and description have been used to refer to like or similar parts of the disclosure.

The drawings and detailed description provide a full and enabling description of the disclosure and the manner and process of making and using it. Each embodiment is provided by way of explanation of the subject matter not limitation thereof. In fact, it will be apparent to those skilled in the art that various modifications and variations may be made to the disclosed subject matter without departing from the scope or spirit of the disclosure. For instance, features illustrated or described as part of one embodiment may be used with another embodiment to yield a still further embodiment.

As illustrated in FIGS. 1-12, a tourniquet 20 for a limb 22 may include an elongated band 24 having a first end 26, a second end 28, and a central portion 30 between first end 26 and second end 28. Elongated band 24 may also have a first edge 32 and a second edge 34 opposite first edge 32 extending between first end 26 and the second end 28.

Elongated band 24 may be made of various different types of materials. For example, elongated band 24 may be formed of a fabric material such as is found in commonly available bandages or wraps used, for example for support and/or compression for sprains, sore muscles, etc., modified as desired for the tourniquet application. Elongated band 24 could be formed of woven natural fibers such as cotton, or synthetics such as woven or non-woven polymers, and/or combinations of materials. Elongated band 24 could be made porous and breathable, or it could be made of a non-breathable barrier-type material. Elongated band 24 could be made of a single-layer material or could be made of multiple layers with similar or dissimilar individual characteristics. Elongated band 24 could also be coated or impregnated with materials for structural purposes, such as providing strengthening, gripping, elasticity, absorbency, wicking, etc., and/or could be coated or impregnated with materials for medical purposes such as an antimicrobial, antiseptic, analgesic, pro-coagulant, etc. Elongated band 24 could have different properties along the band between ends and edges arranged to support the different needs of the different parts of tourniquet 20 during manufacture, stowing, application, or while being worn. For example, surfaces facing the skin may have different properties than surfaces not facing the skin. Also, portions of tourniquet 20 disposed internally or externally before, during or after application may have different properties to suit different needs. Thus, many different types of materials can be used for elongated band 24 in general, and the properties and makeup of elongated band 24 may vary from place to place along the band.

It is desirable that elongated band 24 generally encompass at least one of the following characteristics: lightweight and compact so as to be easy to carry and deploy; strong enough to withstand forces applied during application; elastic so as to stretch during application; and/or tacky so as to cause adjacent winds to cling to each other after application in an at least partially self-gripping frictional fashion to assist in holding the elongated band in place around the limb. Choice of materials may favor one or more of the above characteristics over one or more others. However, many materials would be suitable for elongated band 24.

Some elasticity can be helpful to allow for stretching and tensioning of elongated band 24 during application to the limb, but elasticity is not required in all aspects. If elongated band 24 is elastic, stretching may be up to about 50%, but more preferably up to about 25%, and more preferably up to about 10-20% during application. During application forces applied to elongated band 24 should not cause elongated band 24 to tear. Thus, the band should have enough strength and/or include reinforcement so that tearing does not occur during application which includes some stretching and tensioned winding around the limb. Elongated band 24 should therefore be able to withstand at least about 5 pounds of force, and more preferably at least about 10 pounds of force, and more preferably at least about 20 pounds of force without tearing.

Elongated band 24 generally rectangular, with a width 36 between first and second edges 32, 34 of about 1.0-4.0 inches, more preferably about 2.0-3.5 inches and more preferably about 3.0 inches. Such a width 36 allows elongated band 24 to be rolled into a convenient size for carrying and application that allows for a smooth and flat application on limb 22 without binding or bunching, as discussed below. Thus, having a width 36 of at least about 1.0 inches, and more preferably the widths mentioned above allows for a wide enough application of force to limb 22 to stop bleeding while not being cumbersome to carry or apply. Also, use of a rectangular band spreads force across width 36 to apply desired compression to a larger area of limb 22, whereas substitution with an alternate structure such as a cord, tube or the like having a round or annular cross-section would undesirably concentrate the compression only along the axis of such alternate structure. Width 36 need not be uniform along elongated band between first and second ends 26, 28, as discussed below.

Elongated band 24 defines an opening 38 therethrough between first edge 32 and second edge 34 spaced from first end 26. Opening 38 as illustrated is a thin slit extending most of the way across width 36 to accommodate receiving second end 28 and central portion 30 therethrough (in a manufacturing or set-up step) so as to form a loop 40. Loop 40 (once formed in elongated band 24) begins at opening 38 and ends at a point 41 on elongated band 24 passing through opening 38. Loop 40 should be formed during manufacture or set-up so as to be large enough to comfortably and quickly slide loop 40 over limb 22 to a desired application site. Thus, loop 40 may be at least about 10.0-12.0 inches long for a forearm application, at least about 15.0-18.0 inches for a bicep or calf application, at least about 24.0-30.0 inches for a thigh application. For a universal product, loop 40 can be initially formed at any of the above sizes and quickly modified by sliding elongated band 24 one direction or other relative to opening 38 before or while loop 40 is slid over limb 22 for application. Reinforcement 42 such as the illustrated stitching may be provides adjacent opening 38 to prevent tearing of elongated band during stretching and application to a limb 22.

Elongated band 24 should have a length 37 between first and second ends 26, 28 such that loop 40 and at least two winds, preferably at least three or four winds, can be formed around limb 22, taking into account any material stretching. Thus, elongated band 24 should have a length 37 of at least 30.0 inches, and preferably at least 40 inches or more, for use on an arm, and may be substantially larger if use on a leg is envisioned.

As illustrated, to help achieve a flat and non-gathered orientation or elongated band 24 at opening 38, width 36 of elongated band 24 may vary along the elongated band between the first and second ends 26, 28. In particular, width 36 is greater proximate opening 38 than at least some other locations (i.e., along loop 40) along elongated band 24. If desired, as illustrated loop 40 may have a reduced width 36a, as compared with at least other portions of elongated band 24. If so, the length of opening 38 may be at least substantially equal to (for example, just larger than) width 36a of the elongated band 24 along loop 24. Such structure allows loop 40 to lay flat and not bunch, fold, or gather as it passes through opening 38.

Such flat orientation is achieved in tourniquet 20 by making width 36a of loop 40 less than width 36 adjacent opening 38, which is also the width of the remainder of elongated band 24. In other words, loop 40 is made smaller in width so that it can fit within opening 38 extending partially across an otherwise rectangular elongated band 24. Alternatively (not shown), if loop 40 had a width that was substantially equal to width 36 along elongated band 24, the width of a portion of elongated band 24 in an area adjacent opening 38 could be increased. In such fashion, elongated band would be widened adjacent opening 38 to accommodate a non-reduced size loop portion 40 of elongated band 24. Such varying width and flat, non-gathered orientation can be helpful in some applications but is not however required in all aspects of the invention. Accordingly, elongated band 24 may have a non-varying width 36 between ends 26, 28. Although transitions between widths 36 and 36a are shown as rectangular, such transitions may have other shapes, such as stepped, slanted, curved, etc., to distribute forces as desired along elongated band 24.

As illustrated, a gripping element 44 formed unitarily or in portions may be located at second end 28 of elongated band 24. Gripping element 44 extends at least substantially between first edge 32 and second edge 34. Gripping element 44 is more rigid than the stretchable fabric of elongated band 24 so as to reinforce elongated band 24 and maintain a flat, non-gathered orientation during tightening of the band around limb 22. Thus, as illustrated, gripping element 44 may be a rigid member such as a rod made of wood, plastic, metal, etc. Gripping element 44 may be narrower than width 36 but may alternatively extend at least from first edge 32 to the second edge 34. As illustrated, gripping element 44 extends beyond both edges 32, 34 for ready gripping by the hand of the user not attached to the limb 22 to which tourniquet 20 is being applied.

Gripping element 44 may be held in place on elongated band 24 in various ways. For example, as shown, loop 46 is formed by a row of stitching 48 adjacent first end 26 and gripping element 44 slides into loop 46. Alternatively, adhesives, hook and loop connectors or other methods of attachment may be employed to form loop 46 and/or hold gripping element 44 to first end 26.

Figure 3:
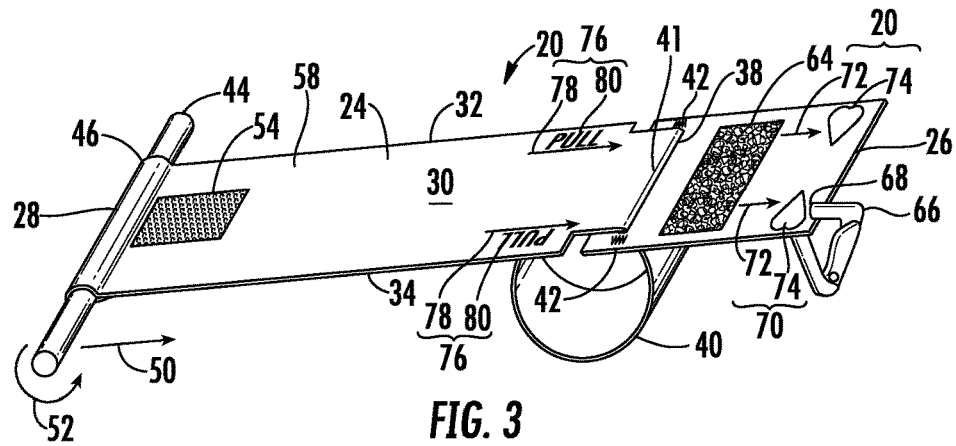
FIG. 3 is an isometric view of the tourniquet of FIG. 1 in an unrolled and looped condition.
Figure 4:
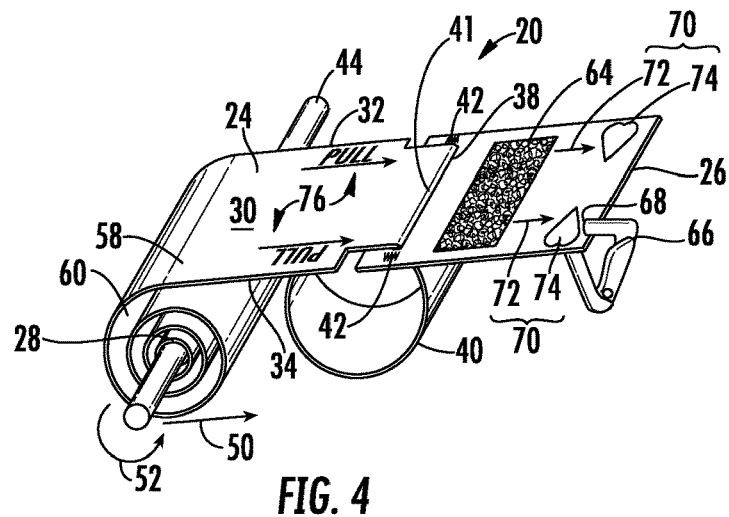
FIG. 4 is an isometric view of the tourniquet of FIG. 1 in a partially rolled and looped condition.

In manufacture or set-up of tourniquet 20, elongated band 24 is wound around gripping element 44. The gripping element 44 is also gripped by a user to wind elongated band 24 around limb. Note arrows 50 and 52 in FIGS. 3 and 4 showing direction of wind-up of elongated band 24 to form the ready to stow or deploy orientation shown in FIG. 5. If desired, as discussed below, gripping element 44 may be detached from elongated band 24 after securement on limb 22, for example by sliding gripping element out of loop 46. Alternatively, gripping element 44 could be permanently attached to elongated band 24 if desired.

Gripping element 44 could alternatively comprise structures other than a rod as shown. For example, gripping element 44 could comprise a gathered, rolled, folded, etc. portion of first end 26, held in place by stitching, adhesive, co-operating hook and loop or snap fasteners, etc. Gripping element 44 could also comprise an additional piece of fabric, coating, plastic or rubber over-mold, etc., at or near first end 26 to strengthen the first end, maintain elongated band 24 in a flat (non-gathered) orientation, and provide a gripping location during winding of elongated band 24 around limb 22. In such case, the gripping element 44 may or may not be wider than width 36 of elongated band 24, although gripping during winding onto limb 22 may be easier if gripping element 44 is wider than elongated band 24. Gripping element 44 of these alternate formations can be formed so that it need not be removed from elongated band 24 after application, if desired.

As illustrated (see FIGS. 1, 2, 10, and 11), tourniquet 20 may include co-operating fastener elements 54, 56, for example disposed along an upper surface 58 and a lower surface 60 of elongated band 24 located proximate second end 28 so as to assist in holding elongated band 24 in place around limb 22 after winding. If desired, co-operating fastener elements 54, 56 may as illustrated include matching fabric hook and loop fasteners (e.g., Velcro® brand). Alternatively, co-operating fastener elements 54, 56 could include at least one of snap fasteners, rigid (metal) hooks and loops, buttons and slots, clips, receivers, an elastic or inelastic loop, etc. Providing such a connection of second end 28 to the next adjacent wind of elongated band 24 around limb 22 holds elongated band in place. Using hook and loop fasteners spaced and sized to allow for a range of final wind sizes allows for essentially infinite adjustability to suit a needed limb (forearm, bicep, calf, thigh) size. Thus, hook and loop fasteners can be sized and placed so as to have suitable overlap for sufficient gripping a final wind suitable for sizes from about 8.0-30.0 inches to accommodate smaller limbs and larger limbs. Some of the other co-operating fastener types above may not have infinite adjustability, and may instead provide multiple attachment orientations (e.g., snap fasteners with multiple differently located female snaps for receiving one or more male snaps to achieve different sizes).

As illustrated (see FIGS. 1, 2, 5, and 6), tourniquet 20 may also include co-operating fastener elements 62, 64 disposed along upper surface 58 and lower surface 60 of elongated band 24 located proximate first end 26 so as to assist in holding the elongated band in a spiral-wound configuration (FIG. 5) with second end 28 in the middle and first end 26 on the outside. As above, such co-operating fastener elements 62, 64 may be fabric hook and loop fasteners or other elements as noted above for co-operating fastener elements 54, 56. Because dimensions of tourniquet 20 in spiral wound configuration of FIG. 5 will be generally known and consistent, co-operating fastener elements 62, 64 can be more precisely located without need for the adjustable differing points of location noted above.

Figure 5:
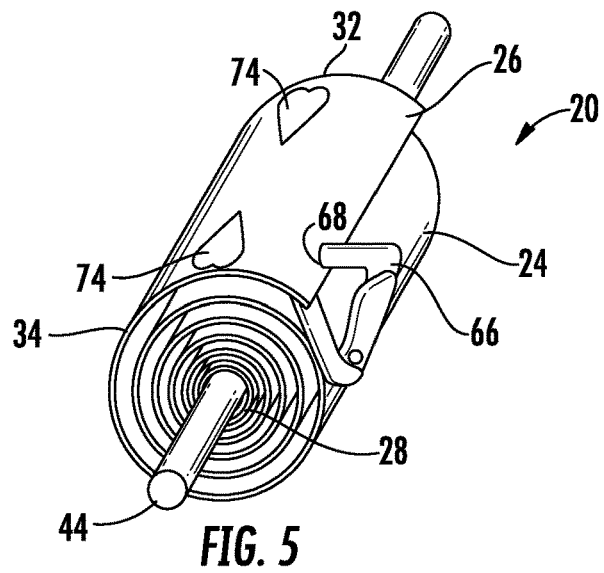
FIG. 5 is an isometric view of the tourniquet of FIG. 1 in a fully rolled and looped condition.
Figure 6:
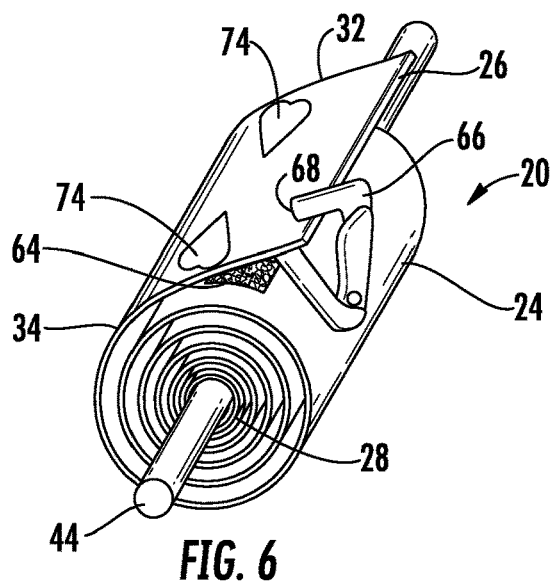
FIG. 6 is an isometric view of the tourniquet of FIG. 1 in a first step of applying the tourniquet in a partially unrolled and looped condition.
Figure 7:
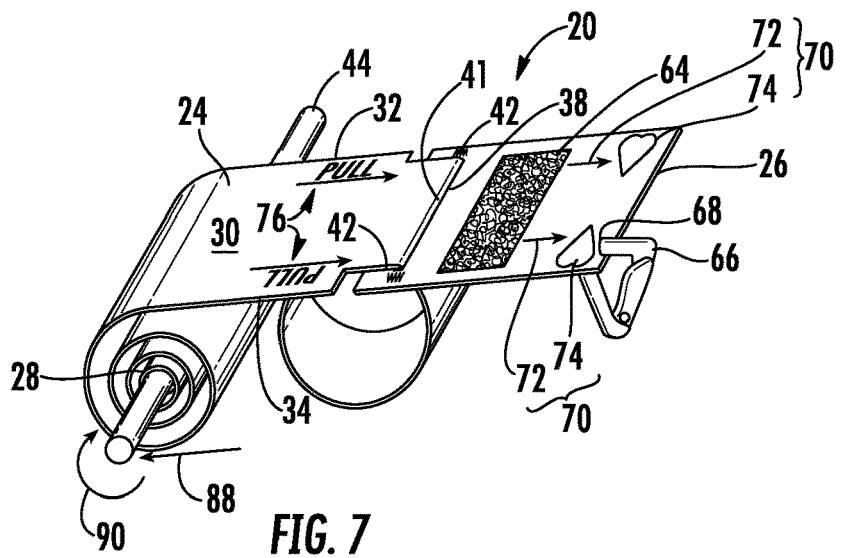
FIG. 7 is an isometric view of the tourniquet of FIG. 1 in a second step of applying the tourniquet in a further unrolled and looped condition.

An attachment member 66 may be secured to elongated band 24 for attaching the elongated band to an external item (such as a clip, loop, etc., on clothing, a storage compartment, etc.) when tourniquet 20 is in the spiral-wound condition of FIG. 5. If desired, attachment member 66 may be a clip such as a carabiner or the like, secured to elongated band 24 proximate first end 26 (for example by extending through an opening 68). Alternatively, attachment member 66 could include or be replaced by other removable or permanent structures (not shown) such as a fabric or elastic material loop, a hook, a portion of a snap or hook and loop fastener, etc. As shown, attachment member 66 is removable from elongated band 24 before, during the process of, or after the sliding on to limb 22 or the winding of elongated band 24 around limb 22. If desired, attachment member 66 can be made generally small enough and out of the way enough that it need not be removed until at least some winds of elongated band 24 are applied to limb 22 so as to not slow or complicate the tourniquet application process, although prior removal is also possible.

Figure 8:
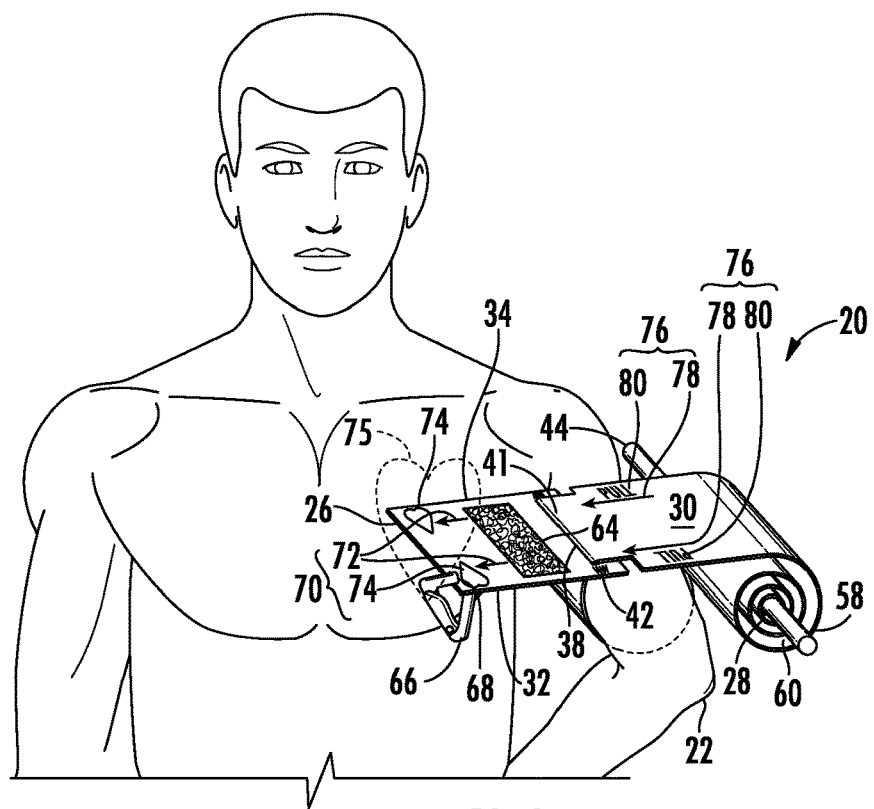
FIG. 8 is an isometric view of the tourniquet of FIG. 1 in a third step of applying the tourniquet in the further unrolled and looped condition, and with the loop slid loosely onto a limb.

If desired, tourniquet 20 may include at least one visible directional indicator to help the user quickly orient tourniquet 20 properly on limb 20. As shown in FIGS. 1 and 3-8, a first visible directional indicator 70 is located on upper surface 58 of elongated band proximate first end 26 to highlight first end 26. Visible directional indicator 70 as illustrated includes indicia such as one or more arrows 72 and hearts 74. When tourniquet is first slid onto limb 22 (such as the left arm as illustrated in FIG. 8), first visible directional indicator 70 highlights first end 26 adjacent loop 40 so help user quickly place tourniquet on the arm in proper orientation (not backwards or upside-down). Indicator 70 intuitively informs the user that first end 26 should point (internally) at the user's heart 75, not external to the user's body, and the upper surface 58 should be oriented upwardly. Alternatively, indicators other than arrows and hearts cold be used, and at different locations visible before or after removal from spiral-wound orientation, to highlight first end 26 to assist with proper orientation.

Figure 9:
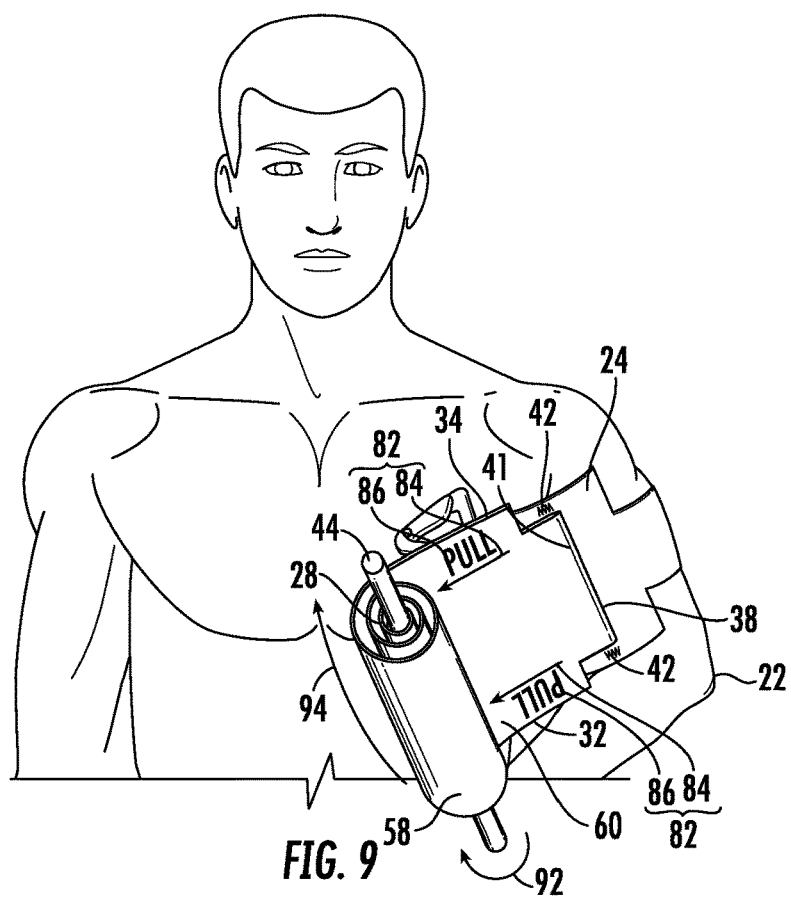
FIG. 9 is an isometric view of the tourniquet of FIG. 1 in a fourth step of applying the tourniquet in the further unrolled and looped condition, and with the loop pulled tightly around the limb.
Figure 10:
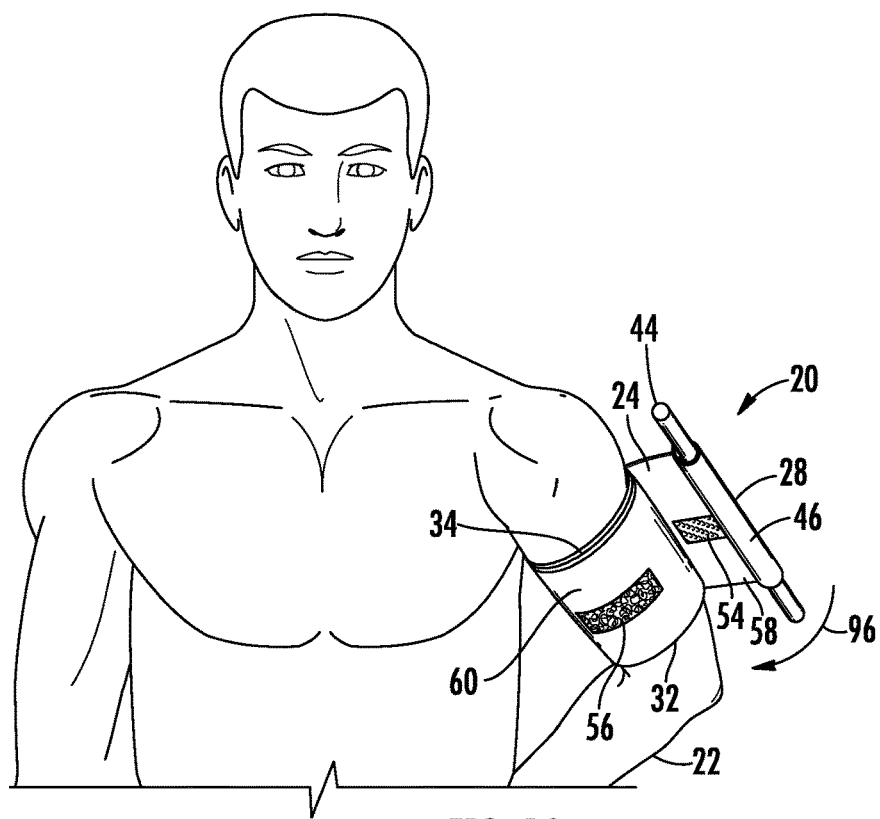
FIG. 10 is an isometric view of the tourniquet of FIG. 1 in a fifth step of applying the tourniquet in a more unrolled and looped condition, and with the tourniquet wound several times around the limb.
Figure 11:
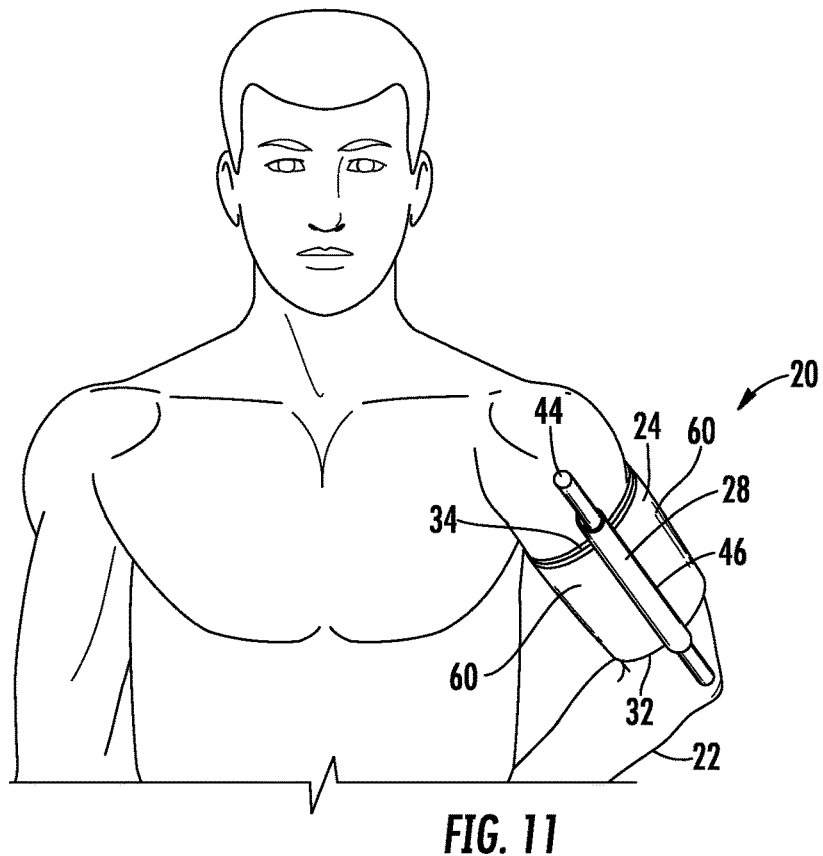
FIG. 11 is an isometric view of the tourniquet of FIG. 1 in a sixth step of applying the tourniquet in a fully unrolled and looped condition, and with the tourniquet end secured to a preceding winding by a fastener.
Figure 12:
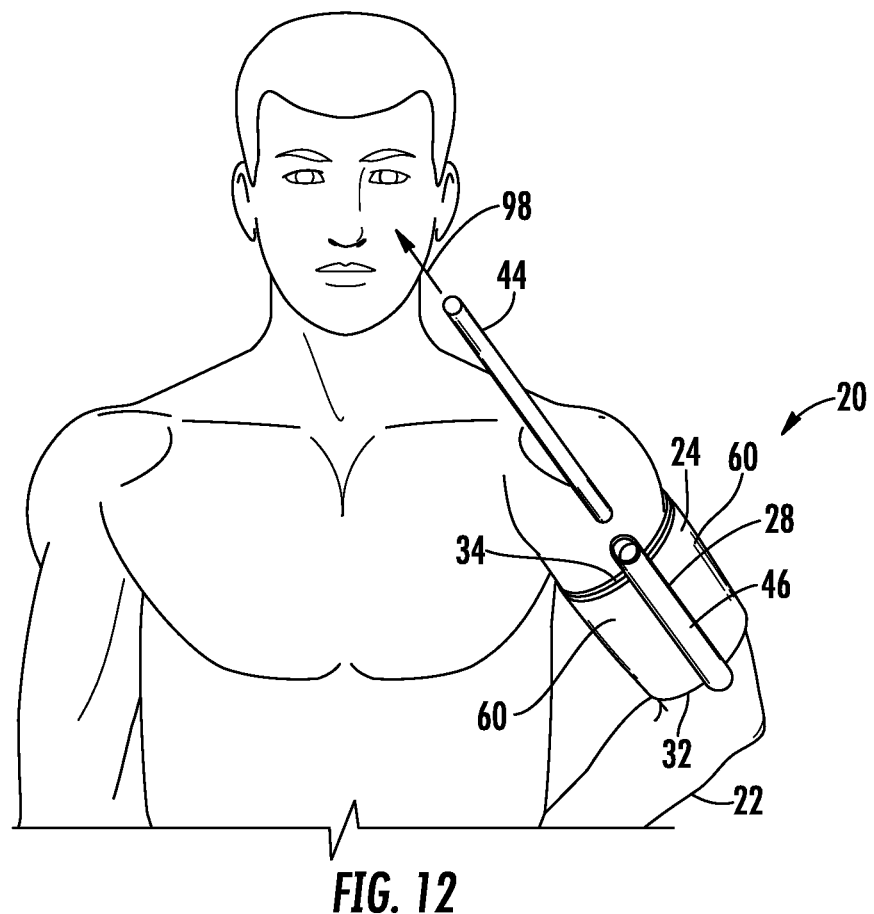
FIG. 12 is an isometric view of the tourniquet of FIG. 1 in a seventh step of applying the tourniquet in the fully unrolled, looped and secured condition, and with a gripping element removed from the band.

If desired one or more additional visible indicators can also be employed to assist the user with tightening and winding elongated band 24 once placed around limb 22. As illustrated in FIGS. 1, 3, 4, and 7-8, a second visible directional indicator 76 is located upper surface 58 near point 41 where band 24 passes into opening 38. As illustrated in FIG. 9, a third visible directional indicator 82 is located on lower surface 60 also near point 41.

As shown, second and third visible directional indicators 76, 82 include respective indicia such as arrows 78, 84 and the word "PULL" 80, 86 between second end 28 and loop 40 to highlight the first end 26. Second directional indicator 76 intuitively informs the user, after elongated band 24 is loosely slid onto limb 22, that the user should first pull second end 28 (and stretch band 24) initially downward toward first end 26 from the position of FIG. 8 toward that of FIG. 9. Once in the position of FIG. 9, elongated band 24 has been redirected about 180 degrees at opening 38 and third visible directional indicator 82 is now visible, thereby telling user to keep pulling and winding elongated band 24 around limb 22 in the same direction.

Such initial downward pull allows loop 40 to tighten and band 24 to begin to wind around limb 22. If the user were to instead pull second end 28 upward from the position of FIG. 8, loop 40 could possibly simply slip (rotate) around limb without gripping or tightening. Thus, the more reliable application direction is a downward pull from the position of FIG. 8, and second visible directional indicator 76 intuitively assists the user with that, after which third visible directional indicator 82 becomes visible again intuitively telling the user to continue winding around limb 22 and pulling to stretch tightly the tourniquet around limb 22.

The steps of rolling up tourniquet 20 into the spiral wound configuration are shown in FIGS. 3-5. This can be done as a last step of manufacturing or by a user. As shown, second end 28 elongated band 24 has been looped though opening 38 and gripping element 44 has been placed in loop 46 so that orientation of tourniquet 20 is as shown in FIG. 3. Gripping element 44 is wound (arrow 52) so as to take up (arrow 50) elongated band 24 around gripping element 44. This process continues through the orientation of FIG. 4, thereafter also rolling up loop 40, to reach the orientation of FIG. 5. Co-operating fasteners 62, 64 are engaged so as to secure first end 26 to the rest of elongated band in the depicted roll form of FIG. 5. Tourniquet 20 can then be attached to a hook, loop or the like by attachment member 66, if desired.

To use tourniquet, first end 26 is pulled so as to separate co-operating fasteners 62, 64 (see FIG. 6), and then elongated band is unrolled toward second end 28 (see arrows 88, 90) but not so far that tourniquet 20 again reaches the orientation of FIG. 3. Instead, elongated band 24 is partially unrolled, and then loop 40 is then slid onto the injured limb 22 using the other hand until tourniquet 20 is in position for tightening (see FIG. 8). The user can grip tourniquet 20 using the hand on the non-injured limb on gripping member 44, and pull downward toward the position shown in FIG. 9. The user can then continue to pull and unwind elongated band (see arrows 92, 94) until fully unwound (see FIG. 10), continuing to pull and stretch to compress the limb sufficient to stop blood flow. The user then pulls second end 28 downward (see arrow 96) so that co-operating elements 54, 56 at second end 28 connect and secure elongated band in place (see FIG. 11). If gripping member 44 is removable, it can be removed (see arrow), although it could be left in place if desired.

Elongated band 24 is thus held in place at least in part by co-operating fasteners 54, 56, and/or frictionally by stretching and tension along surfaces 58, 60 of elongated band 24. No tucking of second end 28 beneath a winding of elongated band 24 is required. No securing of gripping element 44 after winding is required to hold elongated band 24 in place. No step of tightening using a winch, ratchet, windlass, etc. is required after winding, as tensioning and placement occur during winding of elongated band. Dimensioning of elements along elongated band 24 including opening 38 keep elongated band 24 substantially flat during winding. If gripping member 44 is more rigid than elongated band 24, elongated band is more likely to lay flat during winding until the co-operating fasteners 54, 56 engage. Thus, various aspects of tourniquet 20, in combination, sub-combination, or taken separately provide various benefits, such as uncomplicated manufacture, assembly and set-up, quick and reliable single-step placement and tightening on an injured limb, intuitive usage, informational indicia to prevent incorrect usage, and/or ready and reliable securement once wound into place on the limb.

While one or more preferred embodiments of the invention have been described above, it is to be understood that any and all equivalent realizations of the present invention are included within the scope and spirit thereof. The embodiments depicted and described, including alternatives and modifications, are presented by way of example only and are not intended as limitations upon the present invention. Thus, while particular embodiments of the invention have been described and shown, it will be understood by those of ordinary skill in this art that the present invention is not limited thereto since many modifications can be made. Also, elements from different embodiments can be combined or substituted to create still further embodiments following the teachings of this disclosure. Therefore, it is contemplated that any and all such embodiments are included in the present invention as may fall within the literal or equivalent scope of the appended claims.

I claim:

1. A tourniquet for a limb, comprising:
an elongated band having a first end, a second end, and a central portion between the first end and the second end, the elongated band having a first edge and a second edge opposite the first edge extending between the first end and the second end, the elongated band defining an opening therethrough between the first edge and the second edge spaced from the first end but substantially nearer the first end than the second end, the opening configured for receiving the second end and the central portion therethrough so as to form a loop along the elongated band beginning at the opening and ending at a point on the elongated band passing through the opening;
a gripping element at the second end of the elongated band, the gripping element extending at least substantially between the first edge and the second edge, the gripping element being more rigid than the elongated band so as to reinforce the elongated band during tightening of the band around the limb, the gripping element including a rigid member having a length sufficient to extend across the elongated band and past the first edge and the second edge;
first co-operating fastener elements disposed along an upper surface and a lower surface of the elongated band located proximate the second end and substantially nearer the second end than the opening so as to assist in holding the elongated band in place around the limb; and
second co-operating fastener elements disposed along the upper surface and the lower surface located proximate the first end so as to assist in holding the elongated band in a spiral-wound configuration with the second end in the middle and the first end on the outside;
wherein at the first co-operating fastener elements and the second co-operating fastener elements each include respective matching fabric hook and loop fasteners.

2. A tourniquet according to claim 1, wherein the elongated band includes a stretchable material.

3. A tourniquet according to claim 1, wherein the elongated band is formed of a self-gripping material, so that adjacent stretched winds of the elongated band around the limb frictionally grip each other to assist in holding the elongated band in place around the limb.

4. A tourniquet according to claim 1, wherein a width of the elongated band between the first edge and the second edge is substantially equal along the elongated band from the first end to the second end.

5. A tourniquet according to claim 1, wherein a width of the elongated band between the first edge and the second edge varies along the elongated band from the first end to the second end.

6. A tourniquet according to claim 5, wherein the width is greater proximate the opening than at least some other locations along the elongated band from the first end to the second end.

7. A tourniquet according to claim 6, wherein the opening is in the form of a slit having a length.

8. A tourniquet according to claim 7, wherein the length is at least substantially equal to the width of the elongated band at locations between the second end and the opening.

9. A tourniquet according to claim 1, further including an attachment member secured to the elongated band for attaching the elongated band to an external item when the elongated band is in a spiral-wound configuration with the second end in the middle and the first end on the outside.

10. A tourniquet according to claim 9, wherein the attachment member is secured to the elongated band proximate the first end.

11. A tourniquet according to claim 1, further including a first visible directional indicator located on an upper surface of the elongated band proximate the first end to highlight the first end.

12. A tourniquet according to claim 11, wherein a second visible directional indicator is located on one of the upper surface and a lower surface of the elongated band between the second end of the band and the loop to highlight the first end.

13. A tourniquet according to claim 12, wherein a third visible directional indicator is located on the other of the upper surface and the lower surface of the elongated band between the second end of the band and the loop to highlight the first end.

* * * * *